(12) United States Patent
Baxi et al.

(10) Patent No.: US 12,042,259 B2
(45) Date of Patent: *Jul. 23, 2024

(54) NOISE RESILIENT, LOW-POWER HEART RATE SENSING TECHNIQUES

(71) Applicant: Intel Corporation, Santa Clara, CA (US)

(72) Inventors: Amit Sudhir Baxi, Bangalore (IN); Vincent S. Mageshkumar, Navi Mumbai (IN); Indira Negi, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/735,749

(22) Filed: May 3, 2022

(65) Prior Publication Data

US 2022/0257134 A1    Aug. 18, 2022

Related U.S. Application Data

(63) Continuation of application No. 15/781,412, filed as application No. PCT/US2015/066678 on Dec. 18, 2015, now Pat. No. 11,344,213.

(51) Int. Cl.
 *A61B 5/024* (2006.01)
 *A61B 5/00* (2006.01)
 *A61B 5/11* (2006.01)
(52) U.S. Cl.
 CPC ........ *A61B 5/02438* (2013.01); *A61B 5/6803* (2013.01); *A61B 5/1102* (2013.01)
(58) Field of Classification Search
 CPC .. A61B 5/02438; A61B 5/6803; A61B 5/1102
 See application file for complete search history.

(56) References Cited

U.S. PATENT DOCUMENTS

| 5,467,090 A | 11/1995 | Baumgartner et al. |
| 6,431,705 B1 | 8/2002 | Linden |

(Continued)

FOREIGN PATENT DOCUMENTS

| KR | 1020120033530 A | 4/2012 |
| WO | WO-2016077104 A1 | 5/2016 |
| WO | WO-2017105491 A1 | 6/2017 |

OTHER PUBLICATIONS

"U.S. Appl. No. 15/781,412, Final Office Action mailed Sep. 30, 2020", 32 pgs.
"U.S. Appl. No. 15/781,412, Non Final Office Action mailed Mar. 16, 2020", 27 pgs.
"U.S. Appl. No. 15/781,412, Non Final Office Action mailed Jun. 10, 2021", 42 pgs.

(Continued)

*Primary Examiner* — Gary Jackson
*Assistant Examiner* — Sebastian X Lukjan
(74) *Attorney, Agent, or Firm* — Schwegman Lundberg & Woessner, P.A.

(57) ABSTRACT

An apparatus for sensing a heart rate of a subject, including an eyewear frame and a heart rate sensing circuit. The sensing circuit includes first and second piezoelectric sensors configured to be in communication with the subject's skin and to generate first and second voltage signals in response to a periodic vibration in at least one artery of the subject, a first voltage amplifier configured to receive the first voltage signal and output a first amplified voltage signal related to the heart rate of the subject, a second voltage amplifier configured to receive the second voltage signal and output a second amplified voltage signal related to the heart rate of the subject, and a device configured to output a differential signal that is a representation of a difference between the first amplified voltage signal and the second amplified voltage signal that relates to the heart rate.

25 Claims, 4 Drawing Sheets

(56) References Cited

U.S. PATENT DOCUMENTS

| | | | |
|---|---|---|---|
| 7,189,208 B1* | 3/2007 | Beatty | A61B 5/053 600/587 |
| 7,677,723 B2* | 3/2010 | Howell | G02C 11/10 351/158 |
| 11,344,213 B2* | 5/2022 | Baxi | A61B 5/6803 |
| 2004/0215279 A1 | 10/2004 | Houben et al. | |
| 2011/0213271 A1* | 9/2011 | Telfort | A61B 5/7214 600/586 |
| 2014/0194702 A1* | 7/2014 | Tran | A61B 8/565 600/595 |
| 2014/0221772 A1 | 8/2014 | Wolloch et al. | |
| 2015/0003124 A1 | 1/2015 | Sakai et al. | |
| 2015/0305632 A1* | 10/2015 | Najarian | A61B 5/7207 600/479 |
| 2015/0364018 A1 | 12/2015 | Mirov et al. | |
| 2016/0135698 A1 | 5/2016 | Baxi et al. | |
| 2018/0353093 A1 | 12/2018 | Baxi et al. | |

OTHER PUBLICATIONS

"U.S. Appl. No. 15/781,412, Notice of Allowance mailed Feb. 2, 2022", 11 pgs.

"U.S. Appl. No. 15/781,412, Response filed Mar. 30, 2021 to Final Office Action mailed Sep. 30, 2020", 12 pgs.

"U.S. Appl. No. 15/781,412, Response filed Jun. 16, 2020 to Non Final Office Action mailed Mar. 16, 2020", 14 pgs.

"U.S. Appl. No. 15/781,412, Response filed Oct. 12, 2021 to Non Final Office Action mailed Jun. 10, 2021", 17 pgs.

"International Application Serial No. PCT/US2015/066678, International Preliminary Report on Patentability mailed Jun. 28, 2018", 9 pgs.

"International Application Serial No. PCT/US2015/066678, International Search Report mailed Sep. 12, 2016", 3 pgs.

"International Application Serial No. PCT/US2015/066678, Written Opinion mailed Sep. 12, 2016", 7 pgs.

* cited by examiner

NOISE RESILIENT, LOW-POWER HEART RATE SENSING TECHNIQUES

CLAIM OF PRIORITY

This patent application is a continuation of U.S. patent application Ser. No. 15/781,412, filed Jun. 4, 2018, which is a U.S. National Stage Application under 35 U.S.C. 371 from International Application No. PCT/US2015/066678, filed Dec. 18, 2015, published as WO 2017/105491, all of which are incorporated herein by reference in their entirety.

TECHNICAL FIELD

This document pertains generally, but not by way of limitation, to heart rate sensing techniques.

BACKGROUND

Techniques exist to measure heart rate (HR) through a subject's skin using optical sensing. Photoplethysmography (PPG) is one such optical sensing technique. With PPG, light emitting diodes (LEDs) illuminate the skin surface and photodiodes measure minute changes in the light reflected from blood vessels under the skin surface in order to derive a pulsatile signal that is in synchrony with a heartbeat.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that optical sensing techniques such as photoplethysmography (PPG) may not be desirable for continuous long-term monitoring using wearable heart rate monitors, e.g., eyewear, wristbands, etc. For example, sensing techniques such as PPG may utilize high pulsatile peak currents (about 200 milliamps peak) to drive the light emitting diodes (LEDs), which may consume significant energy and may render PPG ineffective for continuous long-term monitoring. For continuous long-term monitoring, large batteries may be needed to power the PPG circuitry. However, large batteries may increase the weight and size of the wearable heart rate monitor, e.g., eyewear, wristbands, etc., which may make them obtrusive, uncomfortable, and unattractive, thereby compromising usability as well as user experience.

In addition, with techniques such as PPG, the front-end circuits to drive the high pulsatile currents through the LEDs may need power metal-oxide-semiconductor field-effect transistors (MOSFETs), large copper traces, which may consume large printed circuit board space, and may generate heat, which may increase the size of the wearable and increase complexity of thermal management. These disadvantages may make it undesirable to use optical sensing techniques with wearable heart rate monitors, e.g., eyewear, wristbands, etc., for continuous long-term monitoring.

Various techniques of this disclosure provide solutions to the above-mentioned problems with PPG, for example, such as by using passive, e.g., zero-power, piezoelectric or pressure-sensitive sensors (also referred to in this disclosure as "piezo sensors" or "piezoelectric transducers") included with a wearable device, e.g., eyewear, wristband, etc., to sense minute pulsatile vibrations in the arteries. For example, one or more piezoelectric sensors may be included with, e.g., coupled to or integral with, the nose pads of eyewear to sense minute pulsatile vibrations in the nasal arteries, e.g., superior labial artery and anterior ethmoidal artery.

Strategically placed piezo sensors may generate a periodic pulse signal from which heart rate may be extracted. The passive piezo sensors do not require any excitation energy and consume significantly less power, e.g., 100 to 1000 times less power, than the power-hungry optical sensors, e.g., LEDs and phototransistors, used in optical PPG techniques. The techniques discussed in this disclosure may utilize small batteries, which may significantly improve the form-factor, weight, aesthetics, usability and user experience. Moreover, in contrast to front-end circuitry of optical PPG, which may include LEDs and phototransistors, the piezo sensors may use a simple front-end circuit, which may further reduce size and cost.

In addition, this disclosure describes techniques for enhancing the signal quality and reliability of wearable heart rate sensors. The present inventors have determined that dual piezo sensors, e.g., mounted on either side of the nose (on both nose pads), may be connected with opposite polarities to generate two independent, complementary but correlated, pulse signal streams. These complementary streams may be fused to improve the pulse signal quality and reliability. The fusion may be done either in the analog domain, e.g. using difference amplification, or in the digital domain using signal processing de-noising techniques, e.g., using cross-correlation, independent component analysis, etc. The resultant fused pulse signal may be much more resilient to motion-induced noise compared to each signal.

In some example implementations, the piezo sensors may be mechanically and electrically mounted such that the pulse signals from two piezo sensors, e.g., from either side of the nose, are 180 degrees out of phase, yet the motion noise picked by the two sensors for certain body movements is in phase. When the two signal streams are subtracted, the resultant pulse signal amplitude may be doubled, whereas the in-phase motion noise may be subtracted (significantly reduced), thereby increasing the Signal-to-Noise ratio (SNR).

Figure 1:
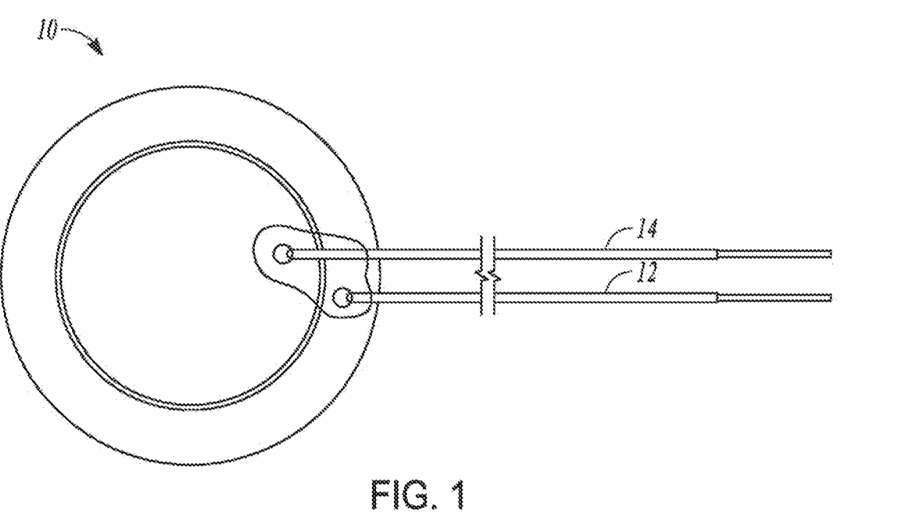
FIG. 1 is an example of a piezoelectric sensor that may be used to implement various techniques of this disclosure.

FIG. 1 is an example of a piezoelectric sensor 10 that may be used to implement various techniques of this disclosure. More particularly, FIG. 1 depicts a piezoelectric disc transducer 10. An example of a disc transducer that may be used to implement various techniques of this disclosure may have a resonant frequency of about 7,000 Hertz. The piezoelectric disc transducer 10 may use a two-wire electrical connection. A first connection 12, e.g., a black wire, may be made to a metallic protective plate on which a piezoelectric crystal is mounted. A second connection 14, e.g., a red wire, may be made to the opposite surface of the crystal. The piezoelectric transducer 10 may be in communication with skin of the subject, e.g., directly or indirectly, and is configured to generate a voltage signal in response to a periodic vibration in at least one artery, the periodic vibration related to the subject's heart rate.

Figure 2:
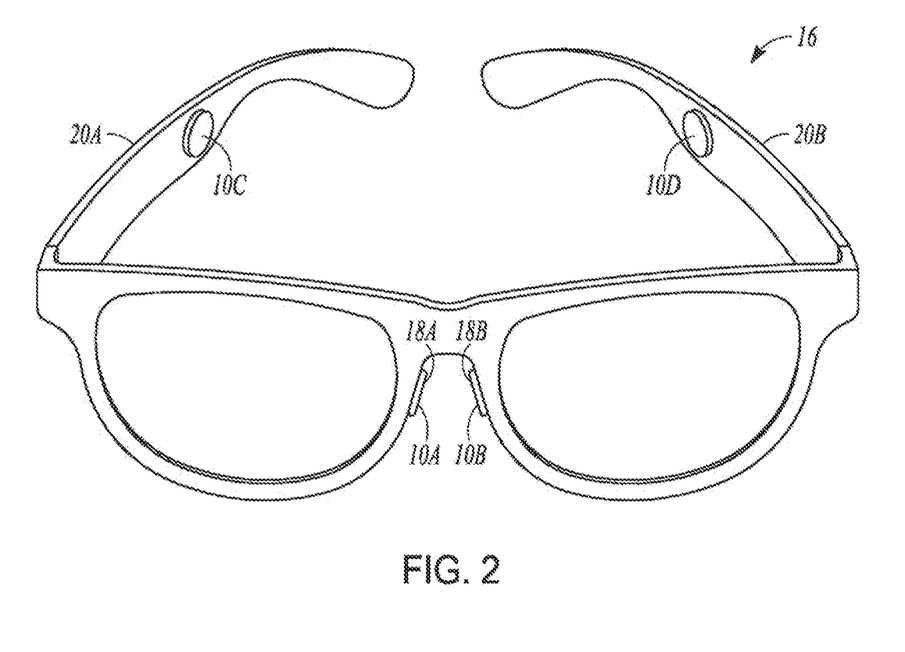
FIG. 2 is an example of an eyewear frame fitted with at least one piezoelectric sensor in accordance with various techniques of this disclosure.

FIG. 2 is an example of an eyewear frame 16 fitted with at least one piezoelectric sensor 10 in accordance with various techniques of this disclosure. In some eyewear implementations, e.g., glasses, goggles, etc., one or more piezoelectric disc transducers 10 may be included with, e.g., coupled to or integral with, the eyewear frame 16. For example, one or both nose pads 18A, 18B (collectively referred to as "nose pads 18") of the eyewear frame 16 (also referred to as "eyewear 16") may include respective piezoelectric disc transducers 10A, 10B (collectively referred to as "piezoelectric disc transducers 10" or "piezo sensors 10").

In an implementation, the piezo sensors 10 may be attached to a substantially non-compressible backing material, e.g., acrylic, which in turn may be attached to the frame 16 of the glasses. In another example, the piezo sensors may be directly molded with the frame or attached to a depression on the nose pads 18. In this manner, the piezoelectric disc transducer(s) 10 may be positioned to sense minute changes in the nasal arteries, e.g. superior labial artery and anterior ethmoidal artery, which may be used to sense a heart rate.

The techniques of this disclosures, however, are not limited to use with nose pads 18 of the eyewear 16. In other example implementations, one or more piezo sensors 10 may be positioned elsewhere on the eyewear frame 16. For example, piezo sensors 10C, 10D may be respectively included with, e.g., coupled to or integral with, one or both of the right and left temples 20A, 20B of the eyewear 16.

Although the piezo sensor 10 does not need to directly touch the skin of the subject, the piezo sensor 10 should generally be included with, e.g., coupled to or integral with, a portion of the wearable, e.g., eyewear frame 16, that does touch skin that is adjacent an artery in order to sense the minute changes in the artery that may be used to sense a heart rate. For example, a nose pad 18 and/or a temple 20 of a pair of glasses may be desirable as these generally contact the skin of a subject.

In addition to piezoelectric disc transducers, the heart rate sensing techniques described in this disclosure may utilize other types of piezo sensors. For example, piezoelectric film may also be used to implement various techniques of this disclosure. As another example, pressure-sensitive paint, e.g., polymer-based, may also be used as a piezo sensor 10.

Figure 3:
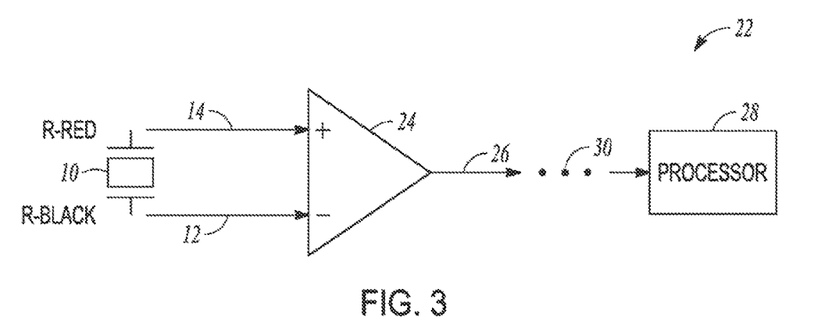
FIG. 3 is an example of a front-end circuit that may be used to implement various techniques of this disclosure.

FIG. 3 is an example of a front-end circuit 22 that may be used to implement various techniques of this disclosure. In FIG. 3, a piezo sensor 10 is in communication with an input of a voltage amplifier 24. The voltage amplifier 24 may be configured to receive a voltage signal generated by the piezo sensor 10 and output an amplified voltage signal 26 related to the heart rate of the subject. An output 26 of the voltage amplifier may ultimately be fed to a processing stage, e.g., processor 28, that may process the signal and derive the heart rate of the subject. Ellipsis 30 indicates that, in some example implementations, additional circuitry, e.g., an analog-to-digital converter, which is beyond the scope of this disclosure, may be included between the amplifier 24 and the processor 28.

Figure 4:
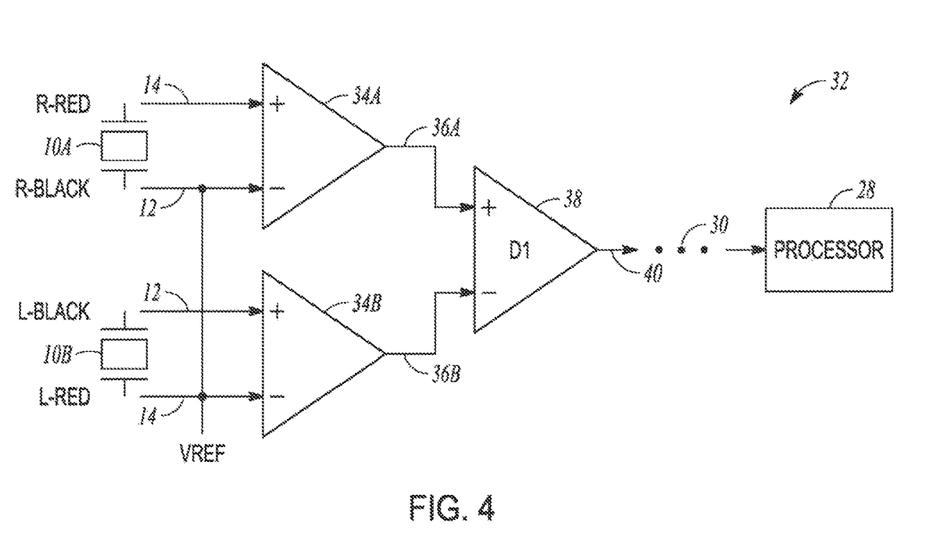
FIG. 4 is another example of a front-end circuit that may be used to implement various techniques of this disclosure.

FIG. 4 is another example of a front-end circuit 32 that may be used to implement various techniques of this disclosure. The front-end circuit 32 of FIG. 4 may be used in example implementations in which at least two piezo sensors 10 are utilized to sense the heart rate of a subject. For example, a first piezo sensor, e.g., piezo sensors 10A or 10C of FIG. 2, may be positioned on a right-hand side of a wearable, e.g., eyeglasses, and a second piezo sensor, e.g., piezo sensors 10B or 10D of FIG. 2, may be positioned on a left-hand side of a wearable, e.g., eyeglasses.

In FIG. 4, a first piezo sensor 10A, e.g., a right piezo sensor, may be in communication with the inputs of a first voltage amplifier 34A. In the example configuration shown in FIG. 4, a first connector 14 of the first sensor 10A, e.g., a red wire, may be in communication with a positive input of the first amplifier 34A and a second connector 12 of the first sensor 10A, e.g., a black wire, may be in communication with a negative input of the first amplifier 34A. A second piezo sensor 10B, e.g., a left piezo sensor, may be connected with opposite polarity to a second voltage amplifier 34B. More particularly, a first connector 12 of the second sensor 10B, e.g., a black wire, may be in communication with a positive input of the second amplifier 34B and a second connector 14 of the second sensor 10B, e.g., a black wire, may be in communication with a negative input of the second amplifier 34B. This arrangement may enable the first and second amplifiers 34A, 34B to generate two independent, complimentary but correlated pulse signals from pulsatile vibrations from a right side and a left side, e.g., on either side of the nose.

The two piezo sensors 34A, 34B may be in communication with skin of the subject and may be configured to generate respective voltage signals in response to a periodic vibration in at least one artery of the subject, the periodic vibration related to the heart rate. The voltage amplifiers 34A, 34B may be configured to receive respective voltage signals generated by the piezo sensors 10A, 10B. Each of the voltage amplifiers 34A, 34B may generate a respective amplified voltage signal 36A, 36B related to the heart rate of the subject. The first amplifier 34A may output a first amplified voltage signal 36A related to the heart rate of the subject and the second voltage amplifier 34B may output a second amplified voltage signal 36B related to the heart rate of the subject.

In the example shown in FIG. 4, VREF may serve as a common voltage reference for the piezo sensors 10A, 10B. In an example implementation, VREF may be about half of a supply voltage, e.g., about half of a 3.3 volt battery voltage. As seen in FIG. 4, the piezo sensors 10A, 10B do not need any power/excitation. Thus, in contrast to a complex optical PPG set up that may consume significant power, e.g., in milliwatts, while giving a single pulse signal, the dual piezo sensor techniques of this disclosure not only consumes about 1000 times less power, e.g., about 2 microwatts, but may provide two independent yet correlated pulse signal streams that may be fused to improve noise resiliency.

The front-end circuitry 32 of FIG. 4 may include a device 38 configured to receive the first amplified voltage signal 36A and the second amplified voltage signal 36B and output a differential signal 40 that is a representation of a difference between the first amplified voltage signal 36A and the second amplified voltage signal 36B, the difference signal related to the heart rate of the subject. The differential calculation may be performed in the analog domain or in the digital domain.

Figure 6:
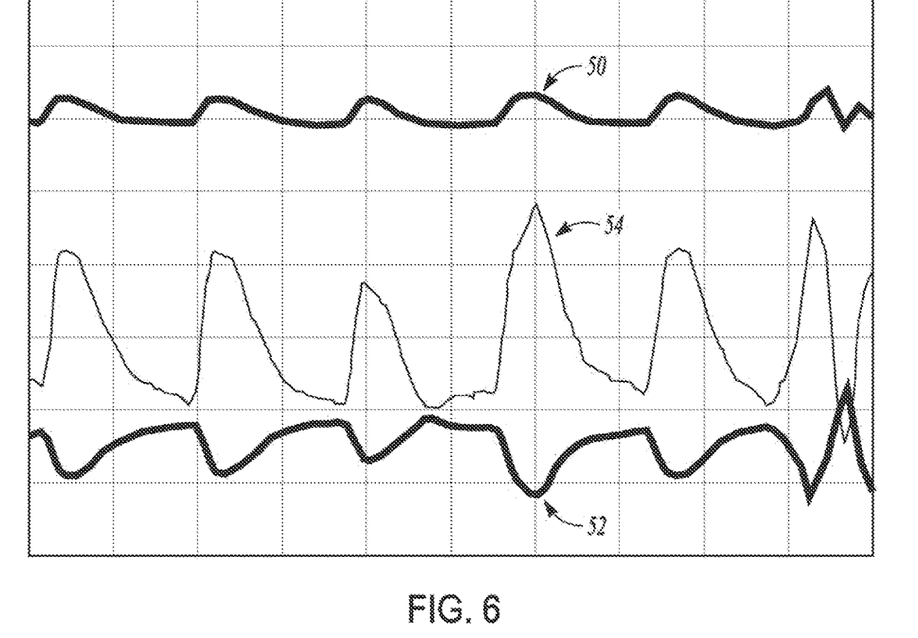
FIG. 6 is an example of a display depicting various output waveforms illustrating the amplified output signals of two piezo sensors and a differential signal using various techniques of this disclosure.
Figure 7:
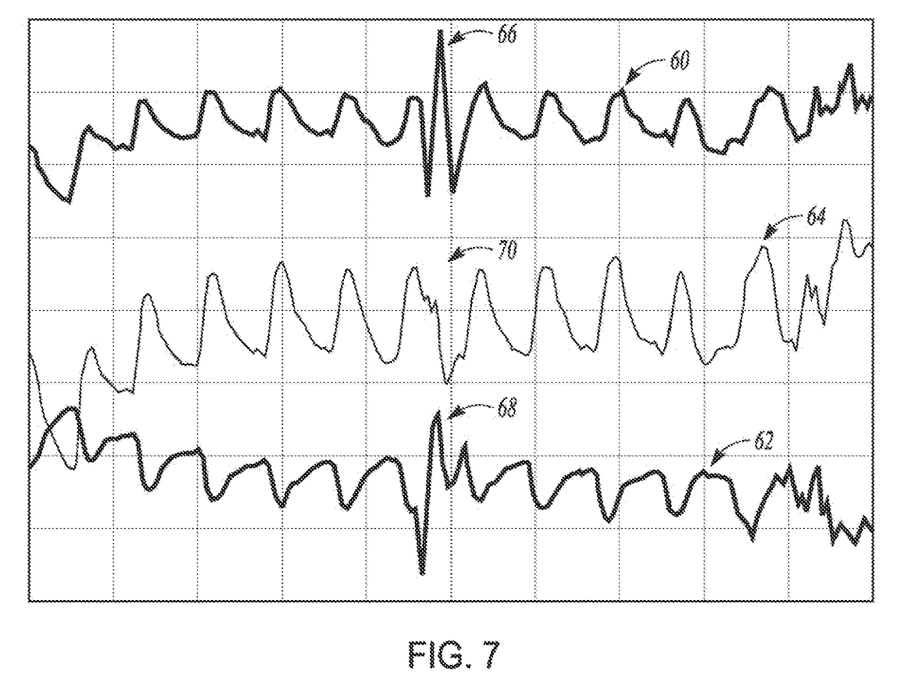
FIG. 7 is another example of a display depicting various output waveforms illustrating the amplified output signals of two piezo sensors and a differential signal using various techniques of this disclosure.
Figure 8:
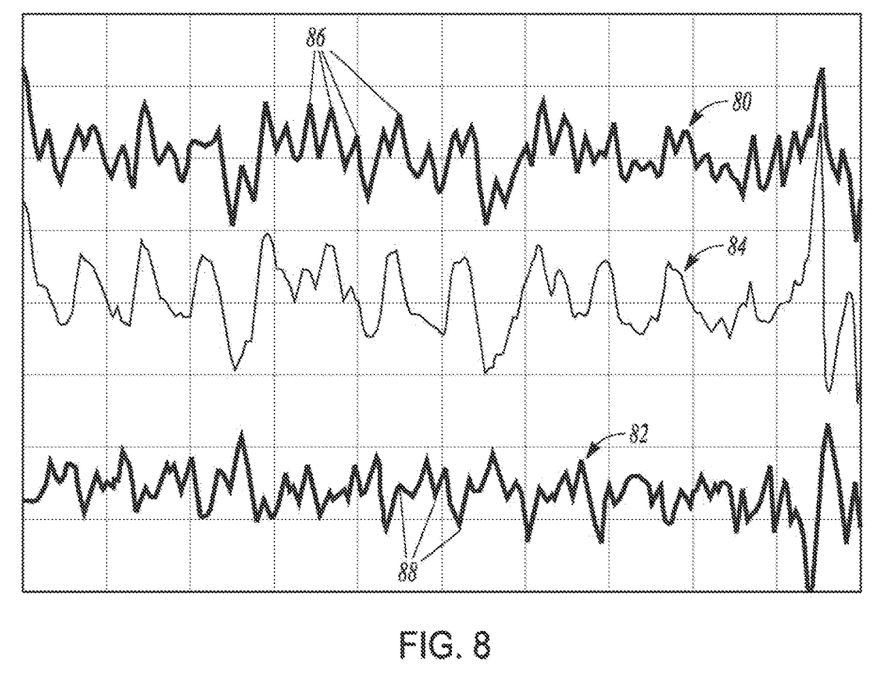
FIG. 8 is another example of a display depicting various output waveforms illustrating the amplified output signals of two piezo sensors and a differential signal using various techniques of this disclosure.

In various example implementations in the analog domain, the device 38 of FIG. 4 may be a differential amplifier. The complimentary signals 36A, 36B may be fused using the differential amplifier 38, which may subtract the signal 36A from the signal 36B to generate a differential signal 40 that relates to the heart rate of the subject. FIGS. 6-8, described in detail below, depict various output waveforms illustrating the output signals 36A, 36B and the differential signal 40. Ellipsis 30 indicates that, in some example implementations, additional circuitry, e.g., an analog-to-digital converter, which is beyond the scope of this disclosure, may be included between the amplifier 38 and the processor 28. The output of the differential amplifier 38 may be digitized, e.g., using an analog-to-digital converter, and then fed to a processor 28 for further processing to extract a periodicity in the pulsatile signal to determine a heart rate of the subject. An example of a differential amplifier that may be used is a TSU 102 operational amplifier available from STMicroelectronics.

Figure 5:
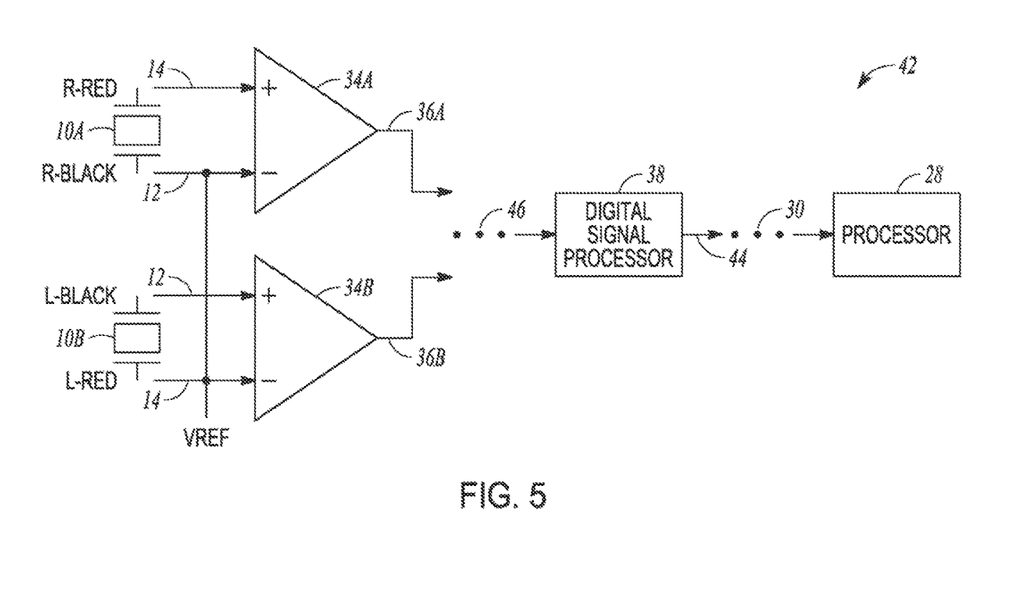
FIG. 5 is another example of another front-end circuit that may be used to implement various techniques of this disclosure.

FIG. 5 is another example of another front-end circuit 42 that may be used to implement various techniques of this disclosure. Many of the components of circuit 42 are similar to those described above with respect to FIG. 4 and, for purposes of conciseness, will not be described again. In various example implementations in the digital domain, the device 38 of FIG. 4 may be a digital device, e.g., a digital signal processor (DSP). Using a digitized representation of the output of piezo sensors 10A, 10B, the device 38 may perform the differential calculation in the digital domain, including signal processing de-noising techniques, e.g., using cross-correlation, independent component analysis, etc. In some examples, the device 38 may output a digital signal 44 that may be fed to a processor 28 for further processing to extract a periodicity in the pulsatile signal to determine a heart rate of the subject. Ellipsis 30 indicates that, in some example implementations, additional circuitry, which is beyond the scope of this disclosure, may be included between the device 38 and the processor 28. Ellipsis 46 indicates that, in some example implementations, additional circuitry, e.g., an analog-to-digital converter, may be included between the amplifiers 34A, 34B and the device 38.

In some example implementations, the processing performed by the processor 28 to extract a periodicity in the pulsatile signal to determine a heart rate of the subject may be performed using circuitry included with, e.g., coupled to or integral with, the wearable, e.g., eyeglasses, wristband. In other example implementations, the processing performed by the processor 28 to extract a periodicity in the pulsatile signal to determine a heart rate of the subject may be performed by external circuitry. For example, data representing the pulsatile signal, e.g., data representing the resultant signal following a differential operation of device 38 of FIGS. 4 and 5, for example, may be transmitted wirelessly, e.g., using Bluetooth® or some other wireless protocol, to an external device, e.g., smartphone, tablet computer, or other computing device, for processing.

In some example implementations, multiple differential pairs, e.g., two or more pairs, of piezo sensors 10 may be used to sense the heart rate of the subject. For example, referring again to FIG. 2, a first pair of piezo sensors 10A, 10B may be included with, e.g., coupled to or integral with, the right and left nose pads 18A, 18B of an eyewear frame 16 and connected to a front-end circuit 32 as shown in FIG. 4. In addition, a second pair of piezo sensors 10C, 10D may be included with, e.g., coupled to or integral with, the right and left temples 20A, 20B of an eyewear frame 16 and connected to another front-end circuit 32. In such an implementation, the two pairs of piezo sensors may provide redundancy in the event that either pair generates a weak signal, for example.

FIG. 6 is an example of a display depicting various output waveforms illustrating the amplified output signals of two piezo sensors and a differential signal using various techniques of this disclosure. The waveforms shown in FIG. 6 were captured when the subject was sitting and wearing eyeglasses, e.g., frames 16 of FIG. 2, under sedentary conditions and using the front-end circuit depicted in FIG. 4.

In FIG. 6, waveform 50 represents an output of a first voltage amplifier in communication with a first piezo sensor included with, e.g., coupled to or integral with, a right nose pad on an eyewear frame, waveform 52 represents an output of a second voltage amplifier in communication with a second piezo sensor included with, e.g., coupled to or integral with, a left nose pad on the eyewear frame, and waveform 54 represents an output of a device, e.g., differential amplifier 38 of FIG. 4, configured to output a differential signal representing a difference between the output of a first voltage amplifier and the output of a second voltage amplifier in communication with a piezo sensor included with, e.g., coupled to or integral with, a right nose pad on an eyewear frame. In other words, waveform 54 represents a difference between waveform 50 and waveform 52.

The waveforms shown in FIG. 6 were generated using the front-end circuit depicted in FIG. 4. As mentioned above, the front-end circuit of FIG. 4 may enable the first and second amplifiers 34A, 34B to generate two independent, complimentary but correlated pulse signals from pulsatile vibrations from a right side and a left side, e.g., on either side of the nose. In a complimentary configuration, when waveform 50 is at a positive peak, the waveform 52 is at a negative peak. These pulsatile signals may be used to estimate a heart rate of a subject.

As seen in FIG. 6, waveforms 50, 52 depict relatively weak pulsatile signals that are contaminated with common-mode noise, e.g., waveforms 50, 52 have thick lines rather than a thin, sharp lines. However, when these complimentary pulse signals 50, 52 are fused, e.g., using a differential amplifier, the resultant waveform 54 is not only stronger in magnitude, e.g., almost twice the amplitude, but also much cleaner, e.g., the waveform 54 may be seen as a sharp, thin line.

FIG. 7 is another example of a display depicting various output waveforms illustrating the amplified output signals of two piezo sensors and a differential signal using various techniques of this disclosure. FIG. 7 illustrates the noise resilience of the complimentary dual piezo sensor arrangement described in this disclosure to head movement. The waveforms shown in FIG. 7 were captured when the subject, while wearing eyewear including piezo sensors in the right and left nose pads and using the front-end circuit depicted in FIG. 4, moved her head suddenly to induce a noise artifact, and then held her head still.

In FIG. 7, waveform 60 represents an output of a first voltage amplifier in communication with a first piezo sensor included with, e.g., coupled to or integral with, a right nose pad on an eyewear frame, waveform 62 represents an output of a second voltage amplifier in communication with a second piezo sensor included with, e.g., coupled to or integral with, a left nose pad on the eyewear frame, and waveform 64 represents an output of a device, e.g., a differential amplifier, configured to output a differential signal representing a difference between the output of a first voltage amplifier and the output of a second voltage amplifier in communication with a piezo sensor included with, e.g., coupled to or integral with, a right nose pad on an eyewear frame. In other words, waveform 64 represents a difference between waveform 60 and waveform 62.

As seen in FIG. 7, waveforms 60, 62 depict relatively weak pulsatile signals and also show prominent noise spikes 66, 68, respectively. Using the dual sensor arrangement shown in FIG. 4, the generated pulse signals 60, 62 are complimentary, e.g., 180 degree out of phase, but the motion noise for certain movements, e.g. due to horizontal left-right head movements, appears in-phase due to inertial effects. Hence, as may be seen in FIG. 7, when the waveforms 60, 62 are fused, e.g., at the differential amplifier 38 of FIG. 4, the resultant signal 64 not only amplifies the complimentary (out of phase) pulse signals 60, 62, but also nullifies the in-phase head motion noise signals 66, 68, as seen at 70 in the resultant waveform 64. This demonstrates the noise resilience of dual sensor arrangement of this disclosure.

FIG. 8 is another example of a display depicting various output waveforms illustrating the amplified output signals of two piezo sensors and a differential signal using various techniques of this disclosure. FIG. 8 illustrates the noise resilience of the complimentary dual piezo sensor arrangement described in this disclosure to head movement. The waveforms shown in FIG. 8 were captured when the subject, while wearing eyewear including piezo sensors in the right and left nose pads and using the front-end circuit depicted in FIG. 4, repetitively moved her head from left to right.

In FIG. 8, waveform 80 represents an output of a first voltage amplifier in communication with a first piezo sensor included with, e.g., coupled to or integral with, a right nose pad on an eyewear frame, waveform 82 represents an output of a second voltage amplifier in communication with a second piezo sensor included with, e.g., coupled to or integral with, a left nose pad on the eyewear frame, and waveform 84 represents an output of a device, e.g., a differential amplifier, configured to output a differential signal representing a difference between the output of a first voltage amplifier and the output of a second voltage amplifier in communication with a piezo sensor included with, e.g., coupled to or integral with, a right nose pad on an eyewear frame. In other words, waveform 84 represents a difference between waveform 80 and waveform 82.

FIG. 8 illustrates several false peaks (head motion noise peaks caused by the rhythmic head movement) superimposed on the heart rate pulse signals sensed independently by the left and right piezo sensors, as shown generally at 86, 88 in waveforms 80, 82, respectively. These false, noise peaks 86, 88 may obscure the true heart rate pulse peaks in the waveforms 80, 82. However, in the resultant signal shown in waveform 84, these head movement noise peaks, which are in-phase, get subtracted. The true heart rate related pulse peaks are much more discernable visually in waveform 84.

Figure 9:
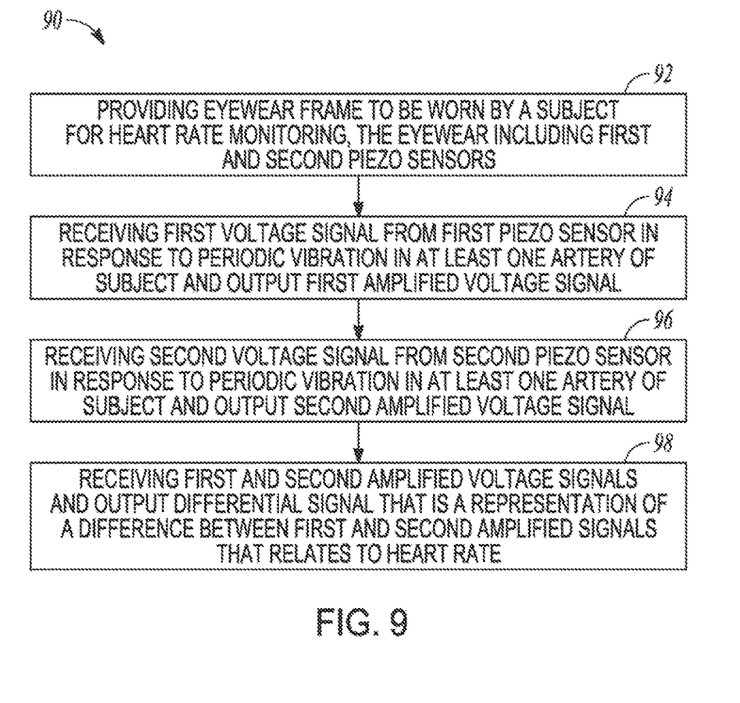
FIG. 9 is an example of a method using various techniques of this disclosure.

FIG. 9 is an example of a method using various techniques of this disclosure. In FIG. 9, the method 90 includes providing an eyewear frame, e.g., frame 16 of FIG. 2, to be worn by a subject for heart rate monitoring, where the eyewear includes first and second piezo sensors, e.g., piezo sensors 10A, 10B of FIG. 4 (block 92). At block 94, the method includes receiving a first voltage signal from the first piezo sensor in response to a periodic vibration in at least one artery of the subject and outputting a first amplified voltage signal, e.g., using amplifier 34A of FIG. 4. At block 96, the method includes receiving a second voltage signal from the second piezo sensor in response to a periodic vibration in at least one artery of the subject and outputting a second amplified voltage signal, e.g., using amplifier 34B of FIG. 4. At block 98, the method include receiving the first and second amplified voltage signals and outputting a differential signal, e.g., using device 38 of FIG. 4 or 5, that is a representation of a difference between the first and second amplified signals that relates to the heart rate of the subject.

In contrast to the optical PPG technique, in which LEDs are excited by about 200 mA peak pulsatile currents and may average power in hundreds of microwatts (μW), the piezo based techniques of this disclosure may consume about 2 microwatts (μW), which is about 100-1000 times less power than the PPG techniques. These techniques may dramatically reduce the battery capacity needed in size-constrained wearables, e.g., eyewear, thereby enabling continuous, long-term monitoring of HR with a small-sized battery.

It should be noted that in some example implementations, various techniques of this disclosure are combinable with optical PPG techniques. For example, heart rate may generally be sensed using the techniques of this disclosure but, if the signals were weak or unavailable, the piezo sensing techniques may be supplemented by the optical PPG techniques, for example. In this manner, power may generally be conserved using the techniques of this disclosure and the optical PPG techniques may be used on an as-needed basis.

Heart rate is an important physiological parameter that may form the basis of inferencing secondary contextual information of the subject, such as emotional state/mood, psychological stress levels, cognitive levels, physical fitness, relaxation, etc. The techniques of this disclosure may make it technically feasible to enable continuous, long-term, unobtrusive HR monitoring in a commonly used wearable, such as eyeglasses. These techniques may enable novel contextual, health or wellness applications.

Various Notes & Examples

Example 1 includes subject matter (such as a device, apparatus, or machine) for sensing a heart rate of a subject, the apparatus comprising: an eyewear frame configured to be worn by the subject; a heart rate sensing circuit configured to sense the heart rate, the heart rate sensing circuit included with the eyewear frame, the heart rate sensing circuit including: a first piezoelectric sensor configured to be in communication with skin of the subject, the first piezoelectric sensor configured to generate a first voltage signal in response to a periodic vibration in at least one artery of the subject, the periodic vibration related to the heart rate; a first voltage amplifier configured to receive the first voltage signal and output a first amplified voltage signal related to the heart rate of the subject; a second piezoelectric sensor configured to be in communication with the skin of the subject, the second piezoelectric sensor configured to generate a second voltage signal in response to the periodic vibration in the at least one artery of the subject; a second voltage amplifier configured to receive the second voltage signal and output a second amplified voltage signal related to the heart rate of the subject; and a device configured to receive the first amplified voltage signal and the second amplified voltage signal and output a differential signal that is a representation of a difference between the first amplified voltage signal and the second amplified voltage signal that relates to the heart rate of the subject.

In Example 2, the subject matter of Example 1 may include, wherein the device is a differential amplifier.

In Example 3, the subject matter of any one or more of Examples 1 to 2 may include, wherein the second amplified voltage signal that is outputted by the second voltage amplifier is 180 degrees out of phase with the first amplified voltage signal that is outputted by the first voltage amplifier.

In Example 4, the subject matter of any one or more of Examples 1 to 3 may include, wherein the eyewear frame includes a first nose pad and a second nose pad, wherein the first piezoelectric sensor is included with the first nose pad, and wherein the second piezoelectric sensor is included with the second nose pad.

In Example 5, the subject matter of any one or more of Examples 1 to 4 may include, wherein the eyewear frame includes a first temple and a second temple, wherein the first piezoelectric sensor is included with the first temple, and wherein the second piezoelectric sensor is included with the second temple.

In Example 6, the subject matter of any one or more of Examples 1 to 5 may include, wherein at least one of the first piezoelectric sensor and the second piezoelectric sensor includes a piezoelectric disc.

In Example 7, the subject matter of any one or more of Examples 1 to 6 may include, wherein at least one of the first piezoelectric sensor and the second piezoelectric sensor includes a piezoelectric film.

In Example 8, the subject matter of any one or more of Examples 1 to 7 may include, wherein at least one of the first piezoelectric sensor and the second piezoelectric sensor includes a pressure-sensitive paint.

Example 9 includes subject matter (such as a circuit) for sensing a heart rate of a subject, the subject matter comprising: a first piezoelectric sensor configured to be in communication with skin of the subject, the first piezoelectric sensor configured to generate a first voltage signal in response to a periodic vibration in at least one artery of the subject, the periodic vibration related to the heart rate; a first voltage amplifier configured to receive the first voltage signal and output a first amplified voltage signal related to the heart rate of the subject; a second piezoelectric sensor configured to be in communication with the skin of the subject, the second piezoelectric sensor configured to generate a second voltage signal in response to the periodic vibration in the at least one artery of the subject; a second voltage amplifier configured to receive the second voltage signal and output a second amplified voltage signal related to the heart rate of the subject; and a device configured to receive the first amplified voltage signal and the second amplified voltage signal and output a differential signal that is a representation of a difference between the first amplified voltage signal and the second amplified voltage signal that relates to the heart rate of the subject.

In Example 10, the subject matter of Example 9 may include, wherein the device is a differential amplifier.

In Example 11, the subject matter of any one or more of Examples 9 to 10 may include, wherein the device is a digital signal processor.

In Example 12, the subject matter of any one or more of Examples 9 to 11 may include, in combination with an eyewear frame configured to be worn by the subject.

In Example 13, the subject matter of any one or more of Examples 9 to 12 may include, wherein the first piezoelectric sensor is included with a first nose pad of the eyewear frame, and wherein the second piezoelectric sensor is included with a second nose pad of the eyewear frame.

In Example 14, the subject matter of any one or more of Examples 9 to 13 may include, wherein the first piezoelectric sensor is included with a first temple of the eyewear frame, and wherein the second piezoelectric sensor is included with a second temple of the eyewear frame.

In Example 15, the subject matter of any one or more of Examples 9 to 14 may include, wherein the second amplified voltage signal that is outputted by the second voltage amplifier is 180 degrees out of phase with the first amplified voltage signal that is outputted by the first voltage amplifier.

In Example 16, the subject matter of any one or more of Examples 9 to 15 may include, wherein at least one of the first piezoelectric sensor and the second piezoelectric sensor includes a piezoelectric disc.

In Example 17, the subject matter of any one or more of Examples 9 to 16 may include, wherein at least one of the first piezoelectric sensor and the second piezoelectric sensor includes a piezoelectric film.

In Example 18, the subject matter of any one or more of Examples 9 to 17 may include, wherein at least one of the first piezoelectric sensor and the second piezoelectric sensor includes a pressure-sensitive paint.

Example 19 includes subject matter (such as an eyewear frame) for sensing a heart rate of a subject, the eyewear frame comprising: a first piezoelectric sensor in communication with skin of the subject, the first piezoelectric sensor configured to generate a first voltage signal in response to a periodic vibration in at least one artery of the subject, the periodic vibration related to the heart rate; a first voltage amplifier configured to receive the first voltage signal and output a first amplified voltage signal related to the heart rate of the subject; a second piezoelectric sensor in communication with the skin of the subject, the second piezoelectric sensor configured to generate a second voltage signal in response to the periodic vibration in the at least one artery of the subject; a second voltage amplifier configured to receive the second voltage signal and output a second amplified voltage signal related to the heart rate of the subject; and a differential amplifier configured to receive the first amplified voltage signal and the second amplified voltage signal and output a differential signal that is a representation of a difference between the first amplified voltage signal and the second amplified voltage signal that relates to the heart rate of the subject.

In Example 20, the subject matter of Example 19 may include, wherein the eyewear frame includes a first nose pad and a second nose pad, wherein the first piezoelectric sensor is included with the first nose pad, and wherein the second piezoelectric sensor is included with the second nose pad.

In Example 21, the subject matter of any one of Examples 19-20 may include, wherein the first piezoelectric sensor is included with a first temple of the eyewear frame, and wherein the second piezoelectric sensor is included with a second temple of the eyewear frame.

In Example 22, the subject matter of any one or more of Examples 19-21 may include, wherein the second amplified voltage signal that is outputted by the second voltage amplifier is 180 degrees out of phase with the first amplified voltage signal that is outputted by the first voltage amplifier.

In Example 23, the subject matter of any one or more of Examples 19-22 may include, wherein at least one of the first piezoelectric sensor and the second piezoelectric sensor includes a piezoelectric disc.

In Example 24, the subject matter of any one or more of Examples 19-23 may include, wherein at least one of the first piezoelectric sensor and the second piezoelectric sensor includes a piezoelectric film.

In Example 25, the subject matter of any one or more of Examples 19-24 may include, wherein at least one of the first piezoelectric sensor and the second piezoelectric sensor includes a pressure-sensitive paint.

Example 26 includes subject matter for sensing a heart rate of a subject (such as a method, means for performing acts, machine readable medium including instructions that when performed by a machine cause the machine to performs acts, or an apparatus configured to perform) comprising: means for generating a first voltage signal in response to a periodic vibration in at least one artery of the subject, the periodic vibration related to the heart rate; means for receiving the first voltage signal and outputting a first amplified voltage signal related to the heart rate of the subject; means for generating a second voltage signal in response to the periodic vibration in the at least one artery of the subject; means for receiving the second voltage signal and outputting a second amplified voltage signal related to the heart rate of the subject; and means for receiving the first amplified voltage signal and the second amplified voltage signal and outputting a differential signal that is a representation of a difference between the first amplified voltage signal and the second amplified voltage signal that relates to the heart rate of the subject.

In Example 27, the subject matter of Example 26 may include, wherein the means for receiving the first amplified voltage signal and the second amplified voltage signal and outputting a differential signal that is a representation of a difference between the first amplified voltage signal and the second amplified voltage signal that relates to the heart rate of the subject is a differential amplifier.

In Example 28, the subject matter of Example 26 may include, wherein the means for receiving the first amplified voltage signal and the second amplified voltage signal and outputting a differential signal that is a representation of a difference between the first amplified voltage signal and the second amplified voltage signal that relates to the heart rate of the subject is a digital signal processor.

In Example 29, the subject matter of any one or more of Examples 26-28 may include, in combination with an eyewear frame configured to be worn by the subject.

In Example 30, the subject matter of any one or more of Examples 26-29 may include, wherein the means for generating a first voltage signal in response to a periodic vibration in at least one artery of the subject is included with a first nose pad of the eyewear frame, and wherein the means for generating a second voltage signal in response to the periodic vibration in the at least one artery of the subject is included with a second nose pad of the eyewear frame.

In Example 31, the subject matter of any one or more of Examples 26-30 may include, wherein the means for generating a first voltage signal in response to a periodic vibration in at least one artery of the subject, and wherein the means for generating a second voltage signal in response to the periodic vibration in the at least one artery of the subject is included with a second temple of the eyewear frame.

In Example 32, the subject matter of any one or more of Examples 26-31 may include, wherein the second amplified voltage signal that is outputted is 180 degrees out of phase with the first amplified voltage signal.

In Example 33, the subject matter of any one or more of Examples 26-32 may include, wherein at least one of the means for generating a first voltage signal in response to a periodic vibration in at least one artery of the subject and the means for generating a second voltage signal in response to the periodic vibration in the at least one artery of the subject includes a piezoelectric disc.

In Example 34, the subject matter of any one or more of Examples 26-33 may include, wherein at least one of the means for generating a first voltage signal in response to a periodic vibration in at least one artery of the subject and the means for generating a second voltage signal in response to the periodic vibration in the at least one artery of the subject includes a piezoelectric film.

In Example 35, the subject matter of any one or more of Examples 26-34 may include, wherein at least one of the means for generating a first voltage signal in response to a periodic vibration in at least one artery of the subject and the means for generating a second voltage signal in response to the periodic vibration in the at least one artery of the subject includes a pressure-sensitive paint.

Example 36 includes subject matter for sensing a heart rate of a subject (such as a method, means for performing acts, machine readable medium including instructions that when performed by a machine cause the machine to performs acts, or an apparatus configured to perform) comprising: generating a first voltage signal in response to a periodic vibration in at least one artery of the subject, the periodic vibration related to the heart rate; receiving the first voltage signal and outputting a first amplified voltage signal related to the heart rate of the subject; generating a second voltage signal in response to the periodic vibration in the at least one artery of the subject; receiving the second voltage signal and outputting a second amplified voltage signal related to the heart rate of the subject; and receiving the first amplified voltage signal and the second amplified voltage signal and outputting a differential signal that is a representation of a difference between the first amplified voltage signal and the second amplified voltage signal that relates to the heart rate of the subject.

In Example 37, the subject matter of Example 36 may include, wherein the outputting a differential signal that is a representation of a difference between the first amplified voltage signal and the second amplified voltage signal that relates to the heart rate of the subject is performed by a differential amplifier.

In Example 38, the subject matter of any one or more of Examples 36-37 may include, wherein the second amplified voltage signal that is outputted is 180 degrees out of phase with the first amplified voltage signal.

In Example 39, the subject matter of any one or more of Examples 36-38 may include, providing an eyewear frame that includes a first nose pad and a second nose pad, the eyewear frame including a first piezoelectric sensor included with the first nose pad, and a second piezoelectric sensor included with the second nose pad, wherein the first piezoelectric sensor is configured to be in communication with skin of the subject, the first piezoelectric sensor configured to generate the first voltage signal, and wherein the second piezoelectric sensor is configured to be in communication with the skin of the subject, the second piezoelectric sensor configured to generate the second voltage signal.

In Example 40, the subject matter of any one or more of Examples 36-39 may include, providing an eyewear frame that includes a first temple and a second temple, the eyewear frame including a first piezoelectric sensor included with the first temple, and a second piezoelectric sensor included with the second temple, wherein the first piezoelectric sensor is configured to be in communication with skin of the subject, the first piezoelectric sensor configured to generate the first voltage signal, and wherein the second piezoelectric sensor is configured to be in communication with the skin of the subject, the second piezoelectric sensor configured to generate the second voltage signal.

In Example 41, the subject matter of any one or more of Examples 39-40 may include, wherein at least one of the first piezoelectric sensor and the second piezoelectric sensor includes a piezoelectric disc.

In Example 42, the subject matter of any one or more of Examples 39-40 may include, wherein at least one of the first piezoelectric sensor and the second piezoelectric sensor includes a piezoelectric film.

In Example 43, the subject matter of any one or more of Examples 39-40 may include, wherein at least one of the first piezoelectric sensor and the second piezoelectric sensor includes a pressure-sensitive paint.

Each of these non-limiting examples may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. An apparatus for sensing a heart rate of a subject, the apparatus comprising:
   an eyewear frame configured to be worn by the subject; and
   a heart rate sensing circuit configured to sense the heart rate, the heart rate sensing circuit included with the eyewear frame, the heart rate sensing circuit including:
   a first piezoelectric sensor configured to be in communication with a first side of a body part of the subject, the first piezoelectric sensor configured to generate a first voltage signal including a first signal portion generated in response to a periodic vibration in at least one artery of the subject, the periodic vibration related to the heart rate;
   a first voltage amplifier configured to receive the first voltage signal with a first polarity and output a first amplified voltage signal related to the heart rate of the subject;
   a second piezoelectric sensor configured to be in communication with a second side of the body part of the subject, the second piezoelectric sensor configured to generate a second voltage signal including a second signal portion generated in response to the periodic vibration in the at least one artery of the subject, the second signal portion out of phase with the first signal portion, the second side of the body part opposite from the first side of the body part;
   a second voltage amplifier configured to receive the second voltage signal with a second polarity opposite to the first polarity and output a second amplified voltage signal related to the heart rate of the subject; and a device configured to receive the first amplified voltage signal and the second amplified voltage signal and generate a fused pulse output signal based on a combination of the first amplified voltage signal and the second amplified voltage signal, the fused pulse output signal indicative of the heart rate of the subject and resilient to motion-induced noise.

2. The apparatus of claim 1, wherein the device is a differential amplifier.

3. The apparatus of claim 1, wherein the second amplified voltage signal that is outputted by the second voltage amplifier is 180 degrees out of phase with the first amplified voltage signal that is outputted by the first voltage amplifier.

4. The apparatus of claim 1, wherein the eyewear frame includes a first nose pad and a second nose pad, wherein the first piezoelectric sensor is included with the first nose pad, and wherein the second piezoelectric sensor is included with the second nose pad.

5. The apparatus of claim 1, wherein the eyewear frame includes a first temple and a second temple, wherein the first piezoelectric sensor is included with the first temple, and wherein the second piezoelectric sensor is included with the second temple.

6. The apparatus of claim 1, wherein at least one of the first piezoelectric sensor and the second piezoelectric sensor includes a piezoelectric disc.

7. The apparatus of claim 1, wherein at least one of the first piezoelectric sensor and the second piezoelectric sensor includes a piezoelectric film.

8. The apparatus of claim 1, wherein at least one of the first piezoelectric sensor and the second piezoelectric sensor includes a pressure-sensitive paint.

9. A heart rate sensing circuit for sensing a heart rate of a subject, the heart rate sensing circuit comprising:
 a first piezoelectric sensor configured to be in communication with a first side of a body part of the subject, the first piezoelectric sensor configured to generate a first voltage signal including a first signal portion generated in response to a periodic vibration in at least one artery of the subject, the periodic vibration related to the heart rate;
 a first voltage amplifier configured to receive the first voltage signal with a first polarity and output a first amplified voltage signal related to the heart rate of the subject;
 a second piezoelectric sensor configured to be in communication with a second side of the body part of the subject, the second piezoelectric sensor configured to generate a second voltage signal with a second polarity opposite to the first polarity including a second signal portion generated in response to the periodic vibration in the at least one artery of the subject, the second signal portion out of phase with the first signal portion, the second side of the body part opposite from the first side of the body part;
 a second voltage amplifier configured to receive the second voltage signal and output a second amplified voltage signal related to the heart rate of the subject; and
 a device configured to receive the first amplified voltage signal and the second amplified voltage signal and generate a fused pulse output signal based on a combination of the first amplified voltage signal and the second amplified voltage signal, the fused pulse output signal indicative of the heart rate of the subject and resilient to motion-induced noise.

10. The heart rate sensing circuit of claim 9, wherein the device is a differential amplifier.

11. The heart rate sensing circuit of claim 9, wherein the device is a digital signal processor.

12. The heart rate sensing circuit of claim 9, in combination with an eyewear frame configured to be worn by the subject.

13. The heart rate sensing circuit of claim 9, wherein the first piezoelectric sensor is included with a first nose pad of an eyewear frame, and wherein the second piezoelectric sensor is included with a second nose pad of the eyewear frame.

14. The heart rate sensing circuit of claim 9, wherein the first piezoelectric sensor is included with a first temple of an eyewear frame, and wherein the second piezoelectric sensor is included with a second temple of the eyewear frame.

15. The heart rate sensing circuit of claim 9, wherein the second amplified voltage signal that is outputted by the second voltage amplifier is 180 degrees out of phase with the first amplified voltage signal that is outputted by the first voltage amplifier.

16. The heart rate sensing circuit of claim 9, wherein at least one of the first piezoelectric sensor and the second piezoelectric sensor includes a piezoelectric disc.

17. The heart rate sensing circuit of claim 9, wherein at least one of the first piezoelectric sensor and the second piezoelectric sensor includes a piezoelectric film.

18. The heart rate sensing circuit of claim 9, wherein at least one of the first piezoelectric sensor and the second piezoelectric sensor includes a pressure-sensitive paint.

19. An eyewear frame configured to be worn by a subject, the eyewear frame comprising:
 a first piezoelectric sensor in communication with a first side of a body part of the subject, the first piezoelectric sensor configured to generate a first voltage signal including a first signal portion generated in response to a periodic vibration in at least one artery of the subject, the periodic vibration related to a heart rate of the subject;
 a first voltage amplifier configured to receive the first voltage signal with a first polarity and output a first amplified voltage signal related to the heart rate of the subject;
 a second piezoelectric sensor in communication with a second side of the body part of the subject, the second piezoelectric sensor configured to generate a second voltage signal with a second polarity opposite to the first polarity including a second signal portion generated in response to the periodic vibration in the at least one artery of the subject, the second signal portion out of phase with the first signal portion, the second side of the body part opposite from the first side of the body part;
 a second voltage amplifier configured to receive the second voltage signal and output a second amplified voltage signal related to the heart rate of the subject; and
 a differential amplifier configured to receive the first amplified voltage signal and the second amplified voltage signal and generate a fused pulse output signal based on a combination of the first amplified voltage signal and the second amplified voltage signal, the fused pulse output signal indicative of the heart rate of the subject and resilient to motion-induced noise.

20. The eyewear frame of claim 19, wherein the eyewear frame includes a first nose pad and a second nose pad, wherein the first piezoelectric sensor is included with the first nose pad, and wherein the second piezoelectric sensor is included with the second nose pad.

21. The eyewear frame of claim 19, wherein the first piezoelectric sensor is included with a first temple of the eyewear frame, and wherein the second piezoelectric sensor is included with a second temple of the eyewear frame.

22. A method for sensing a heart rate of a subject, the method comprising:
generating a first voltage signal with a first polarity including a first signal portion generated in response to a periodic vibration in a first artery in a first side of a body part of the subject, the periodic vibration related to the heart rate;
receiving the first voltage signal and outputting a first amplified voltage signal related to the heart rate of the subject;
generating a second voltage signal with a second polarity opposite to the first polarity including a second signal portion generated in response to the periodic vibration in a second artery in a second side of the body part of the subject, the second signal portion out of phase with the first signal portion, the second side of the body part opposite from the first side of the body part;
receiving the second voltage signal and outputting a second amplified voltage signal related to the heart rate of the subject; and
receiving the first amplified voltage signal and the second amplified voltage signal and generating a fused pulse output signal based on a combination of the first amplified voltage signal and the second amplified voltage signal, the fused pulse output signal indicative of the heart rate of the subject and resilient to motion-induced noise.

23. The method of claim 22, wherein the second amplified voltage signal that is outputted is 180 degrees out of phase with the first amplified voltage signal.

24. The method of claim 22, further comprising providing an eyewear frame that includes a first nose pad and a second nose pad, the eyewear frame including a first piezoelectric sensor included with the first nose pad, and a second piezoelectric sensor included with the second nose pad, wherein:
the first piezoelectric sensor is configured to be in communication with skin of the subject, the first piezoelectric sensor configured to generate the first voltage signal; and
the second piezoelectric sensor is configured to be in communication with the skin of the subject, the second piezoelectric sensor configured to generate the second voltage signal.

25. The method of claim 22, comprising:
providing an eyewear frame that includes a first temple and a second temple, the eyewear frame including a first piezoelectric sensor included with the first temple, and a second piezoelectric sensor included with the second temple,
wherein the first piezoelectric sensor is configured to be in communication with skin of the subject, the first piezoelectric sensor configured to generate the first voltage signal, and wherein the second piezoelectric sensor is configured to be in communication with the skin of the subject, the second piezoelectric sensor configured to generate the second voltage signal.

* * * * *